United States Patent

Schmid et al.

US005763086A

[11] Patent Number: 5,763,086
[45] Date of Patent: Jun. 9, 1998

[54] GONIOCHROMATIC LUSTER PIGMENTS WITH SILICON-CONTAINING COATING

[75] Inventors: Raimund Schmid, Neustadt; Norbert Mronga, Dossenheim; Jörg Adel, Ludwigshafen, all of Germany

[73] Assignee: BASF Aktiengesellschaft, Ludwigshafen, Germany

[21] Appl. No.: 728,375

[22] Filed: Oct. 9, 1996

[30] Foreign Application Priority Data

Oct. 14, 1995 [DE] Germany .................. 195 38 295.1

[51] Int. Cl.$^6$ .............. B32B 5/16; B05D 7/00; D02G 3/00
[52] U.S. Cl. .............. 428/404; 427/213; 427/216; 427/220; 427/229; 427/255.6; 427/372.2; 427/385.5; 427/387; 427/388.1; 428/447
[58] Field of Search ............... 428/403, 424, 428/447; 427/213, 216, 220, 229, 255.6, 372.2, 385.5, 387, 388.1

[56] References Cited

U.S. PATENT DOCUMENTS

| | | | |
|---|---|---|---|
| 3,438,796 | 4/1969 | Hanke | 106/291 |
| 4,328,042 | 5/1982 | Ostertag et al. | 106/308 B |
| 4,344,987 | 8/1982 | Ostertag et al. | 427/213 |
| 4,879,140 | 11/1989 | Gray et al. | 427/38 |
| 4,978,394 | 12/1990 | Ostertag et al. | 106/404 |
| 5,352,286 | 10/1994 | Schmid et al. | 106/404 |
| 5,364,467 | 11/1994 | Schmid et al. | 106/404 |
| 5,374,306 | 12/1994 | Schlegel et al. | 106/404 |
| 5,472,640 | 12/1995 | Bruckner et al. | 252/518 |
| 5,474,605 | 12/1995 | Schmid et al. | 106/404 |
| 5,505,991 | 4/1996 | Schmid et al. | 427/215 |
| 5,565,024 | 10/1996 | Schrami-Marth | 106/415 |
| 5,607,504 | 3/1997 | Schmid et al. | 106/403 |
| 5,624,486 | 4/1997 | Schmid et al. | 106/404 |
| 5,662,738 | 9/1997 | Schmid et al. | 106/404 |

FOREIGN PATENT DOCUMENTS

| | | |
|---|---|---|
| 0 033 457 | 8/1981 | European Pat. Off. . |
| 0 045 851 | 2/1982 | European Pat. Off. . |
| 0 338 428 | 10/1989 | European Pat. Off. . |
| 42 23 384 | 1/1994 | Germany . |
| 42 36 332 | 5/1994 | Germany . |
| 43 13 541 | 10/1994 | Germany . |
| 43 40 141 | 6/1995 | Germany . |
| 44 05 492 | 8/1995 | Germany . |
| 44 14 079 | 10/1995 | Germany . |
| 44 19 173 | 12/1995 | Germany . |
| 44 37 752 | 4/1996 | Germany . |

Primary Examiner—H. Thi Le
Attorney, Agent, or Firm—Oblon, Spivak, McClelland, Maier & Neustadt, P.C.

[57] ABSTRACT

Goniochromatic luster pigments based on multiply coated platelet-shaped metallic substrates comprising at least one layer packet of A) a layer consisting essentially of silicon oxide, silicon oxide hydrate, aluminum oxide and/or aluminum oxide hydrate, and B) a nonselectively absorbing, silicon-containing layer which is at least partially transparent to visible light, and also, if desired, additionally C) an outer layer which consists essentially of colorless or selectively absorbing metal oxide, are useful for coloring paints, inks, including printing inks, plastics, glasses, ceramic products and decorative cosmetic preparations.

10 Claims, No Drawings

GONIOCHROMATIC LUSTER PIGMENTS WITH SILICON-CONTAINING COATING

FIELD OF THE INVENTION

The present invention relates to novel goniochromatic luster pigments based on multiply coated platelet-shaped metallic substrates comprising at least one layer packet of A) a layer consisting essentially of silicon oxide, silicon oxide hydrate, aluminum oxide and/or aluminum oxide hydrate, and B) a nonselectively absorbing, silicon-containing layer which is at least partially transparent to visible light, and also, if desired, additionally C) an outer layer which consists essentially of colorless or selectively absorbing metal oxide.

The invention further relates to mixtures of pigments (I) and multiply coated silicatic platelets (II) comprising A') a layer consisting essentially of colorless or selectively absorbing metal oxide, B') a nonselectively absorbing, silicon-containing, metallic layer which is at least partially transparent to visible light, and if desired C') an outer layer which consists essentially of colorless or selectively absorbing metal oxide, as essential components.

The invention also relates to the production of the goniochromatic luster pigments and to their use for coloring paints, inks, including printing inks, plastics, glasses, ceramic products and decorative cosmetic preparations.

DESCRIPTION OF THE BACKGROUND

Luster effect pigments are used in many sectors of industry, for example in automotive coatings, decorative coating, plastics pigmentation, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Owing to their uncopyable optical effects, these pigments are increasingly gaining in importance for the production of forgeryproof security documents, such as banknotes, checks, check cards, credit cards, tax stamps, postage stamps, rail and air tickets, telephone cards, lottery tickets, gift vouchers, passes and identity cards.

Markings prepared with the luster effect pigments and the absence of these markings or their alteration, for example in a color copy (disappearance of color flops and luster effects), are reliably discernible by the unaided, naked eye and so make it easy to distinguish the copy from the original.

Metallic substrate luster pigments, having high hiding power, are also of particular interest for automotive coatings.

Hitherto the metallic substrate luster pigments used for this purpose have been iron oxide-coated aluminum pigments, as described in EP-A-33 457, which exhibit strong golden to red reflection colors at the specular angle, but look achromatic at steeper viewing angles. To obtain coatings with a two-tone effect, these pigments are therefore mixed with color pigments of a different color.

Goniochromatic pigments, which exhibit an angle-dependent color change between different interference colors, ie. bring about a two-tone effect in coatings or prints even without the addition of other pigments, are known from, for example, U.S. Pat. No. 3,438,796, which describes symmetrically constructed pigments consisting of a central opaque aluminum film (60 nm in thickness) coated on both sides with a thick $SiO_2$ film (500 nm), a transparent aluminum film (20 nm), and a thin $SiO_2$ film (200 nm).

These pigments are produced by vapor deposition of $SiO_2$ and aluminum alternately in a high vacuum. The multilayered film deposited in this manner is then removed from the substrate film, for example by scratching it off, and comminuted to particle sizes typical of luster pigments (about 5–50 μm).

Owing to the manner of manufacture, the central metal film of these pigments is coated only on the platelet top and bottom, and each platelet is therefore only incompletely protected from the environment or the attack of chemicals. In addition, the manufacturing process is also very complicated and costly.

U.S. Pat. No. 4,879,140 describes a process wherein vaporized metal compounds are decomposed in the gas phase under the action of a microwave plasma and the decomposition products are deposited in a film on the reactor wall. Silicon films are obtained for example by decomposing $SiH_4$, and $SiO_2$ films by decomposing silicon tetrachloride, in the presence of oxygen. The deposited films can be comminuted to pigment size by a number of measures. However, the pigments thus obtainable likewise have the abovementioned disadvantages.

Furthermore, DE-A-44 05 492 discloses goniochromatic luster pigments wherein aluminum platelets are initially coated wet-chemically with silicon oxide by hydrolytic decomposition of organosilicon compounds and then with metallic layers, such as molybdenum-, iron- or chromium-containing layers, by gas phase coating through chemical vapor deposition (CVD). Generally, these pigments have to be coated with a passivating layer to increase their fastness properties, in particular the condensation water resistance. DE-A-44 19 173, unpublished at the priority date of the present invention, describes magnetizable luster pigments wherein the aluminum platelets are additionally coated with an inner ferromagnetic layer. German Patent Application 19516181.5 discloses similar luster pigments having a metallic coating consisting essentially of aluminum.

DE-A-44 3.7 752, unpublished at the priority date of the present invention, discloses a CVD process whereby the $SiO_2$ layer can also be applied by gas phase decomposition of organosilicons.

It is an object of the present invention to provide goniochromatic luster pigments which are free of the disadvantages mentioned and have advantageous application properties.

SUMMARY OF THE INVENTION

We have found that this object is achieved by the above-described luster pigments and their mixtures with multiply-coated silicatic platelets.

We have also found a process for producing these luster pigments, which comprises coating the metallic substrate platelets with layers (A) by gas phase decomposition of volatile organosilicons using water vapor and/or oxygen or by hydrolytic decomposition of organic silicon or aluminum compounds in which the organic radicals are attached to the metal via oxygen atoms in the presence of an organic solvent in which the metal compounds are soluble and which is miscible with water, and subsequent drying, layers (B) by gas phase decomposition of silanes of the formula I $$Si_nX_{2n+2} \qquad \qquad I$$

where n is from 1 to 3, and

X is hydrogen or identical or different $C_1$–$C_3$-alkyl when n=1, at least one X being hydrogen, or is hydrogen when n>1, with or without metal carbonyls in an inert atmosphere and if desired layer (C) by gas phase decomposition of volatile metal compounds in the presence of oxygen and/or water vapor Finally, the present invention also provides for the use of these luster pigments and luster pigment mixtures for coloring paints, inks, including printing inks, plastics, glasses, ceramic products and decorative cosmetic preparations.

DETAILED DESCRIPTION OF THE INVENTION

Suitable metallic substrates for the luster pigments of the present invention include all metals and alloys in platelet form known for metallic effect pigments. Examples besides steel, copper and its alloys such as brass and bronzes include in particular aluminum and its alloys such as aluminum bronze.

Preference is given to aluminum flakes which are producible in a simple manner by the stamping out of aluminum foil or by common atomizing and grinding techniques.

Suitable aluminum platelets are produced for example by the Hall process by wet grinding in white spirit. The starting material is an atomized, irregular aluminum grit which is ball-milled in white spirit and in the presence of lubricant into platelet-shaped particles and subsequently classified.

Commercial products can be used. However, the surface of the aluminum particles should be substantially free of fats or other coating media. These substances can to some extent be removed by solvent treatment or better, as described in DE-A-42 23 384, by oxidative treatment.

Furthermore, the metallic substrate particles may have been given a passivating treatment, ie. may have been given a coating which confers resistance especially against water, as known for example from DE-A-42 36 332 and DE-A-44 14 079, which was unpublished at the priority date of the present invention.

The term "passivating coatings" also encompasses metal oxide layers. Examples of further suitable substrates are therefore iron oxide-coated metal pigments (eg. EP-A-33 457) having a (weak) golden to red self-color and delicately pastel-colored titania-coated metal pigments (eg. EP-A-338 428). However, the metal oxide layer should not be too thick in order that the substrate particles may retain their "metallic coloristics".

Other suitable substrate materials are finally magnetizable aluminum platelets which comprise a ferromagnetic, iron-, cobalt-, nickel-, magnetite- or γ-$Fe_2O_3$-containing coating (DE-A-43 13 541, DE-A-43 40 141 and DE-A-44 19 173, which was unpublished at the priority date of the present invention) and make it possible to produce magnetizable goniochromatic luster pigments.

The size of the substrate particles is not critical per se and can be adapted to the particular use. In general, the particles have average largest diameters from about 1 to 200 μm, in particular from about 5 to 100 μm, and thicknesses from about 0.1 to 5 μm, in particular round about 0.5 μm. Their specific free surface area (BET) is generally within the range from 0.1 to 5 $m^2$/g.

The luster pigments of the present invention have a multiple coating on the metallic substrate.

Layer (A) includes as essential constituents aluminum oxide, aluminum oxide hydrate and preferably silicon oxide and silicon oxide hydrate and also mixtures thereof.

The thickness of the layer (A) is generally within the range from 20 to 800 nm, preferably within the range from 50 to 600 nm. Since layer (A) essentially determines the hue of the pigments of the present invention, it has a minimum thickness of about 100 nm for the preferred luster pigments which have only a layer packet (A)+(B) and a particularly pronounced color play.

As the thickness of layer (A) increases, in the case of pigments coated with layer (A) and metallic layer (B) an observer at a viewing angle of 25° will see the interference color change repeatedly in succession from blue to green to gold to red. The angle dependence of the hue increases from the first interference color series to higher series (ie. to thicker layers (A)). The second interference color series starts at a layer thickness of about 275 nm and the third series at about 450 nm. The interference colors of the third series are extremely angle-dependent. For instance, a pigment which reflects green in a direct, plan view undergoes a color change via blue to red at an increasingly flat angle.

The absorbing layer (B) consists essentially of silicon or mixtures of silicon and other metals which are depositable by gas phase decomposition of the carbonyls, such as molybdenum, chromium, tungsten and iron. These mixtures generally also include the respective silicides. Particular preference is given to mixtures of silicon and molybdenum, which customarily include molybdenum silicide $MoSi_2$. In general, the silicon content of the mixed layers (B) is from about 5 to 90% by weight, preferably from 8 to 80% by weight, particularly preferably from 30 to 60% by weight. Such layers (B) are notable for high fastness properties, including in particular high condensation water resistance.

Layer (B) should be at least partially transparent (semitransparent) to visible light and therefore generally has a layer thickness of from about 5 to 30 nm. For layers (B) which comprise silicon and molybdenum thicknesses of from about 5 to 20 nm are preferred, while "pure" silicon layers (B) preferably have thicknesses of from 20 to 30 nm.

If a plurality (eg. 2, 3 or 4) of layer packets (A)+(B) are present, then layer (A) is preferably from 20 to 400 nm and layer (B) is preferably from 2 to 5 nm in thickness. However, preference is given to luster pigments having only a layer packet of (A)+(B).

The luster pigments of the present invention may further include an outer layer (C) for additional variation of the color properties.

Layer (C) is preferably formed from high refractive index metal oxides which can be not only colorless but also selectively absorbing. Examples of prepared metal oxides include titanium dioxide, zirconium oxide, iron(III) oxide and chromium(III) oxide.

The thickness of layer (C) is generally from about 1 to 400 nm, preferably from 5 to 250 nm. For example, for $Fe_2O_3$- and $Cr_2O_3$-containing layers (C) thicknesses of from 1 to 20 nm and for $TiO_2$- and $ZrO_2$-containing layers (C) thicknesses of up to 100 nm are preferred.

Layer (C) contributes to the interference color of the pigment and continues the interference color series at the point determined by the substrate coated with (A) and (B).

Colored metal oxides such as iron oxide and chromium oxide will with their absorption color modify, and with increasing thickness ultimately obscure, the interference color of the multilayer system.

In the luster pigments of the present invention, all layers are altogether noticeable for their uniform, homogeneous and filmlike construction and their interference capability even at relatively high thicknesses, resulting in strong interference color multilayer systems in which the substrate particles are coated on all sides, not only on the platelet surface and subface.

Coloristically, mixtures of the novel metallic pigments (I) with likewise multiply coated silicatic platelets (II) are also of particular interest.

Particularly preferred silicate-based substrates are light-colored and white micas, and flakes of preferably wet-ground muscovite are particularly preferred. Of course, it is also possible to use other natural micas such as phlogopite and biotite, artificial micas, and talc and glass flakes.

The silicate-based substrate particles used have a metal oxide layer (A') which is preferably constructed from high refractive metal oxides such as titanium oxide, zirconium oxide, zinc oxide, tin oxide, chromium oxide, iron oxide and/or bismuth oxychloride. Aluminum oxide and silicon oxide may likewise be present.

Particular preference is given to mica pigments comprising a layer (A') which consists essentially of titanium dioxide and includes the other oxides mentioned at most in a minor amount.

Metal oxide-coated silicate-based pigments are generally known and are also commercially available under the designations of Iriodin® (Merck, Darmstadt), Flonac® (Kemira Oy, Pori) or Mearlin® (Mearl Corporation, New York).

Suitable choice of the silicate-based pigments (II) will vary or complement the color play of the metal pigments (I).

If, for instance, a metallic substrate coated with (A) and (B) has a golden hue at a viewing angle of 25°, this golden hue can be shifted toward a more reddish hue by mixing the metal pigment coated only with (A) with titania-coated mica pigments having a reddish golden interference color and subsequent conjoint coating with (B).

The composition of the luster pigment mixtures of the present invention is determined by the desired coloristics.

In principle the weight ratio of metallic pigment (I): silicate-based pigment (II) can be varied within the range from 1:99 to 99:1. To obtain adequate hiding power, the pigment mixtures of the present invention preferably include at least 5% by weight of metallic luster pigment (I).

The preferred way of producing the pigment mixtures of the present invention is the conjoint coating of the substrate particles already coated with layer (A) and a layer (A') in the course of step (a) with the metallic layer (B) and if desired the cover layer (C).

Of course, however, all layers can be applied separately and the coated pigments can then be mixed afterwards. This procedure provides the additional option of variation of layers (B) and (B') and also (C) and (C').

In the novel process for producing the luster pigments, the individual layers are applied by gas phase decomposition of suitable volatile metal compounds (chemical vapor deposition, CVD) or wet-chemically by hydrolytic decomposition of especially organic metal compounds.

Of course, the two methods can be combined in any desired way for producing the individual layers.

The silicon and/or aluminum oxide layers (A) are equally producible using the wet-chemical method and the CVD method, but the CVD method will usually be preferable.

In the wet-chemical process described in DE-A-44 05 492, organic silicon and/or aluminum compounds in which the organic radicals are bonded to the metals via oxygen atoms are hydrolyzed in the presence of the substrate particles and of an organic solvent in which the metal compounds are soluble.

The preferred embodiment is to hydrolyze the metal alkoxides (especially tetraethoxysilane and aluminum triisopropoxide) in the presence of an alcohol (especially isopropanol) and of aqueous ammonia as catalyst.

This is preferably done by initially charging substrate particles, isopropanol, water and ammonia, heating this mixture to from 40° C. to 80° C., especially to from about 60° C. to 70° C., with stirring and continuously adding a solution of the metal alkoxide in isopropanol. Following a subsequent stirring time of usually from 1 to 15 h. the mixture is cooled down to room temperature, and the coated pigment is isolated by filtering off, washing and drying.

In the CVD process described in DE-A-44 37 752, unpublished at the priority date of the present invention, silanes which contain at least one alkanoyloxy radical are decomposed in the gas phase with water vapor and, if the silanes also contain alkyl or phenyl radicals, oxygen in the presence of agitated substrate particles.

Preferred silanes are alkoxy and alkanoyloxy radicals; di-tert-butoxydiacetoxysilane is particularly preferred.

To carry out the CVD process, it is advisable, as is generally the case for CVD processes, to use a fluidized bed reactor as described for example in EP-A-45 851. The substrate particles are heated in the reactor to the desired reaction temperature (generally from 100° to 600° C., preferably from 150° to 300° C.) under fluidization with an inert gas such as nitrogen, and silane and water vapor (and optionally oxygen) are then introduced with the aid of inert carrier gas streams (advantageously part-streams of the fluidizing gas) from upstream vaporizer vessels via separate nozzles. Silane concentration is advantageously held at ≦5% by volume, preferably ≦2% by volume, based on the total amount of gas in the reactor. The amount of water vapor required for the decomposition depends on the concentration of the silane and should correspond at least to the amount stoichiometrically required for hydrolysis, but preference is given to an amount from 10 to 100 times that amount.

The silicon-containing layers (B) are applied in the manufacturing process of the present invention by gas phase decomposition of silanes. If said layers (B) are to contain other metals as well as silicon, the silanes are decomposed simultaneously with the corresponding metal carbonyls.

Suitable for this purpose are silanes of the formula $$Si_nX_{2n+2} \qquad \qquad I$$

where n is from 1 to 3, and X is hydrogen or identical or different $C_1$–$C_3$-alkyl when n=1, at least one X being hydrogen, or is hydrogen when n>1.

As well as mono-, di- and trialkylsilanes such as dimethylsilane, it is advantageous to use in particular the purely hydrogen-containing silanes monosilane ($SiH_4$), trisilane ($Si_3H_8$) and preferably disilane ($Si_2H_6$).

Advantageously, the silicon-containing layers (B) are applied by transferring the silane from a pressurized gas flask together with an inert gas stream (especially argon) via a preferably temperature-controlled nozzle into the coating reactor and thermally decomposing it there at from 100° to 600° C., preferably at from 150° to 500° C., thereby depositing a silicon film on the agitated (A)-coated substrates in the reactor. The gas quantity of silane should generally not exceed more than 2% by volume, preferably not more than 1% by volume, of the total amount of gas in the reactor.

If the layers (B) are to consist of mixtures of silicon and other metals, a second opening into the reactor is used to admit a further inert gas stream passed first through an upstream vaporizer vessel containing the corresponding metal carbonyl and load it in this way with metal carbonyl vapor. Metal carbonyl and silane then decompose simultaneously in the reactor and become deposited on the substrate particles as a mixed silicon/metal layer or as a metal silicide film.

The preferred reactor is in particular the abovementioned fluidized bed reactor, but it is also possible to use a single-neck round-bottom flask made of quartz glass which is rotated by a motor, provided with gas inlet and outlet lines in the axis of rotation and heated by a clamshell oven (rotary sphere oven).

In principle the reactor used can be any heatable mixer which agitates the substrate particles gently by means of appropriate internal fitments and permits the supply and removal of gas.

For a continuous process on an industrial scale it is also possible to use, for example, a rotary tube furnace to which the substrate particles and the silane/inert gas mixture (and metal cabonyl/inert gas mixture) are fed continuously.

Outer metal oxide layers (C) are applied in the process of the present invention by well known oxidative gas phase decomposition of the metal carbonyls (eg. iron pentacarbonyl, chromium hexacarbonyl) or hydrolytic gas phase decomposition of the metal alkoxides (eg. titanium and zirconium tetra-n- and -isopropoxide) (EP-A-33 457, EP-A-338 428).

The manufacturing process of the present invention provides a simple way of reproducibly producing large amounts of multiply coated luster pigments. The pigment particles obtained are completely enclosed by coatings whose individual layers are of high quality (homogeneous, filmlike).

The luster pigments and luster pigment mixtures of the present invention are advantageously useful for many purposes, such as the coloring of plastics, glasses, ceramic products, decorative cosmetic preparations and particularly coatings, especially automotive coatings, and inks, especially security printing inks. All customary printing processes can be employed, for example screen printing, intaglio printing, bronze printing, flexographic printing and offset printing.

The pigments of the present invention are also advantageously useful for these purposes in admixture with transparent and hiding wet, colored and black pigments and also commercial transparent, colored and black luster pigments based on metal oxide-coated mica and metal pigments, platelet-shaped iron oxides, graphite, molybdenum sulfide and platelet-shaped organic pigments.

EXAMPLES

Preparation and application of luster pigments according to the present invention To incorporate the pigments into a paint, 0.4 g in each case of pigment was dispersed in 3.6 g of a mixed-polyester varnish having a solids content of 21% by weight and the mixture was dispersed in a red devil for 2 min. Drawdowns of the pigmented varnishes were knife-coated onto black and white cardboard at a wet film thickness of 160 μm. The water resistance of the coatings was tested by knife-coating them onto transparent polyester films and immersing these in water for a prolonged period.

To apply the pigments in screen printing, 10 g of pigment were stirred into 90 g of a commercially available binder solution (22.5 g of PVC copolymer Laroflexe® MP45, 4.5 g of methoxypropyl acetate, 13.5 g of n-hexyldiglycol, 49.5 g of butylglycol). The screen printing ink thus prepared was applied with a commercially available screen printing machine (screen mesh size from 112 to 150 μm) to coated, titania-coated paper in a thickness of 45 μm and air-dried.

Example 1 a) In a round-bottom flask equipped with reflux condenser and stirrer, 100 g of finely divided aluminum powder (average particle diameter 20 μm) were suspended in 1.5 l of isopropanol. After addition of 400 ml of water and 40 ml of a 25% strength by weight aqueous ammonia solution, the suspension was heated to 65° C. with vigorous stirring. At the same time the metered addition was commenced of a mixture of 600 ml of isopropanol and 600 g of tetraethoxysilane (rate of addition 100 ml/h, 12 h). Following a subsequent stirring time of 10 h and cooling, the product was filtered off, is thoroughly washed with isopropanol and dried at 80° C.

The coated aluminum powder had a silicon content of 26.7% by weight and a slightly greenish tinge.

b) 50 g of the coated aluminum powder were then heated in the above-described rotary sphere reactor to 500° C. following a two-hour inertization with 20 l/h of argon. 8.5 l/h of disilane were then transferred from a pressurized gas flask in a mixture with argon (10% by volume of disilane in gas mixture) via a nozzle at 300° C. into the reactor and decomposed there to silicon and hydrogen. The addition of silane was terminated after 1 h. The reactor was kept at 500° C. for an additional 2 h, then cooled down to room temperature and aired.

The pigment obtained had a total silicon content of 28.8% by weight, so that the silicon coating (B) accounts for 2.1% of the weight of the pigment.

On application in a paint and in screen printing, the pigment exhibited strong metallic luster combined with an intensively greenish golden interference color which flopped into a greenish tinge at steeper viewing angles. A color copy of the screen print produced using a commercial color copier (Canon CLC 500) did not show any angle-dependent color play, only showing a combination shade.

Example 2 a) 200 g of the finely divided aluminum powder were suspended in 1 l of isopropanol in the apparatus of Example 1. The suspension was heated to 80° C. with vigorous stirring. At the same time the metered addition was commenced of 1350 g of tetraethoxysilane and, also at the same time, a mixture of 860 ml of water, 86 ml of 25% strength by weight aqueous ammonia solution and 400 ml of isopropanol. The rate of addition was in both cases 100 ml/h; the addition was complete after 14 h. Following a subsequent stirring time of 10 h, the mixture was worked up as in Example 1.

The coated aluminum-powder had a silicon content of 28.2% by weight and exhibited a slightly greenish shimmer.

b) 30 g of the coated aluminum powder were then heated to 450° C. in the rotary sphere oven inertized as in Example 1. Then, over a period of 7 h, 10 l/h disilane were transferred into the reactor via a nozzle at 100° C. in a mixture with argon (10% by volume of disilane in the gas mixture), and, at the same time (likewise over 7 h), via a further inlet, 5 g of molybdenum hexacarbonyl, were carried by a nitrogen stream of 20 l/h, and decomposed in the reactor into a silicon/molybdenum mixture, hydrogen and CO. The reactor was held at 450° C. for a further 2 h, then cooled down to room temperature and aired.

The pigment obtained had a molybdenum content of 1.3% by weight and a total silicon content of 32.8% by weight, so that the silicon content of layer (B) accounts for 5.0% of the weight of the pigment.

On application in a paint and in screen printing, the pigment exhibited strong metallic luster combined with an intensively green interference color which flopped toward red at steeper viewing angles.

Example 3

200 g of the $SiO_2$-coated aluminum pigment of Example 2a) were heated to 300° C. in the fluidized-bed reactor under fluidization with 600 l/h of nitrogen. A gas mixture of 0.3 l/h of disilane, 2.7 l/h of-argon and 200 l/h of nitrogen was passed in via one of the side nozzles over a period of 7 h. At the same time, via the other side nozzle, 25 g of molybdenum hexacarbonyl were transferred into the reactor, by means of a 400 l/h nitrogen stream, from a reservoir temperature-controlled at 70° C., likewise over 7 h. The reactor was then held at 300° C. for a further 2 h, then cooled down to room temperature while a further 600 l/h of nitrogen were passed in, and aired.

The pigment obtained had a molybdenum content of 3.4% by weight and a total silicon content of 27.5% by weight, so that the silicon content of layer (B) accounts for 0.3% of the weight of the pigment.

On application in a paint and in screen printing, the pigment exhibited strong metallic luster combined with an intensively green interference color which flopped toward red at steeper viewing angles.

Comparative example 180 g of the $SiO_2$-coated aluminum pigment of Example 2a) was coated with molybdenum similarly to Example 3 but without the addition of silane.

On application, the pigment obtained exhibited an intensively blue interference color which flopped toward red at steeper viewing angles.

A water resistance test on a coating comprising this pigment produced decoloration overnight, while coatings comprising pigments of Examples 1 to 3 were free of any decoloration even several days later.

We claim:

1. Goniochromatic luster pigments based on multiple coated platelet-shaped metallic substrates having a multiple coating comprising at least one layer packet of A) a layer consisting essentially of silicon oxide, silicon oxide hydrate, aluminum oxide and/or aluminum oxide hydrate, and B) a nonselectively absorbing, silicon-containing layer which is at least partially transparent to visible light, and optionally C) an outer layer which consists essentially of colorless or selectively absorbing metal oxide.

2. Luster pigments as claimed in claim 1 wherein layer (B) consists essentially of silicon or of mixtures of silicon, other metals and/or silicides of these metals.

3. Luster pigments as claimed in claim 1 wherein layer (B) consists essentially of silicon, of mixtures of silicon with molybdenum, chromium, tungsten and/or iron and/or silicides of these metals.

4. Luster pigments as claimed in claim 1 wherein layer (C) comprises titanium dioxide, zirconium dioxide, iron(III) oxide and/or chromium(III) oxide.

5. Luster pigments as claimed in claim 1 comprising only one layer packet (A)+(B).

6. Luster pigments as claimed in claim 1 wherein the metallic substrate consists essentially of aluminum platelets produced by common atomizing and grinding techniques.

7. Luster pigments as claimed in claim 1 wherein the metallic substrate consists essentially of aluminum platelets which may be coated with a ferromagnetic layer and/or passivated.

8. Luster pigment mixtures of

I) the luster pigments of claim 1, and

II) multiply coated silicate-based platelets comprising

A') a layer consisting essentially of colorless or selectively absorbing metal oxide, B') a nonselectively absorbing, silicon-containing, metallic layer which is at least partially transparent to visible light, and optionally C') an outer layer which consists essentially of colorless or selectively absorbing metal oxide, as essential components.

9. A process for producing luster pigments as claimed in claim 1, which comprises coating the platelet-shaped metallic substrates with layer (A) by gas phase decomposition of volatile organosilicons using water vapor and/or oxygen or by hydrolytic decomposition of organic silicon or aluminum compounds in which organic radicals are attached to the silicon or aluminum via oxygen atoms in the presence of an organic solvent in which the silicon or aluminum compounds are soluble and which is miscible with water, and subsequent drying, layers (B) by gas phase decomposition of silanes of the formula I $$Si_nX_{2n+2} \quad (I)$$

where n is from 1 to 3, and each X is independently hydrogen or $C_1$–$C_3$-alkyl when n=1, at least one X being hydrogen, or is hydrogen when n>1, with or without metal carbonyls in an inert atmosphere and optionally layer (C) by gas phase decomposition of volatile metal compounds in the presence of oxygen and/or water vapor.

10. A process for coloring paints, inks, plastics, glasses, ceramic products and decorative cosmetic preparations which comprises using luster pigments as claimed in claim 1.

* * * * *